United States Patent [19]

Mason

[11] Patent Number: 5,001,272

[45] Date of Patent: Mar. 19, 1991

[54] PROCESS FOR THE PRODUCTION OF DINITROTOLUENE

[75] Inventor: Robert W. Mason, Lake Charles, La.

[73] Assignee: Olin Corporation, Cheshire, Conn.

[21] Appl. No.: 402,322

[22] Filed: Sep. 5, 1989

Related U.S. Application Data

[63] Continuation-in-part of Ser. No. 210,549, Jun. 22, 1988 now pending.

[51] Int. Cl.$^5$ .................................................. C07C 205/06
[52] U.S. Cl. ........................................ 568/934; 568/932
[58] Field of Search ............................ 568/932, 927, 934

[56] References Cited

U.S. PATENT DOCUMENTS

| | | | |
|---|---|---|---|
| 2,362,743 | 11/1944 | Crater | 568/934 |
| 2,739,174 | 3/1956 | Ross | 260/645 |
| 2,864,871 | 12/1958 | Morningstar | 568/932 |
| 3,261,908 | 4/1961 | Schroeder et al. | 260/369 |
| 3,434,802 | 3/1969 | Toischer et al. | 23/260 |
| 3,780,116 | 12/1973 | Sahgal | 260/645 |
| 3,928,395 | 12/1975 | Seha et al. | 568/937 X |
| 3,957,889 | 5/1976 | Milligan et al. | 568/932 X |
| 3,976,704 | 8/1976 | Vaughan | 260/645 |
| 4,036,838 | 7/1977 | Vogel et al. | 568/932 X |
| 4,064,147 | 12/1977 | Thelen et al. | 260/369 |
| 4,112,005 | 9/1978 | Thiem et al. | 260/645 |
| 4,123,466 | 10/1978 | Lin et al. | 260/645 |
| 4,347,389 | 8/1982 | Schumacher et al. | 568/937 |
| 4,415,744 | 11/1983 | Schumacher | 560/20 |
| 4,418,230 | 11/1983 | Bakke et al. | 568/940 |
| 4,426,543 | 1/1984 | Schumacher et al. | 568/940 |
| 4,465,876 | 8/1984 | Milligan | 568/940 |
| 4,469,904 | 9/1984 | Wang et al. | 568/948 |
| 4,551,568 | 11/1985 | Sato et al. | 568/939 |
| 4,600,702 | 7/1986 | Schumacher | 502/200 |
| 4,618,733 | 10/1986 | Schumacher | 568/927 |
| 4,628,131 | 12/1986 | Schumacher | 568/937 |
| 4,804,792 | 2/1989 | Mason et al. | 568/927 X |

Primary Examiner—Robert L. Stoll
Assistant Examiner—Valerie D. Fee
Attorney, Agent, or Firm—Dale Lynn Carlson

[57] ABSTRACT

Aromatic nitration reactions and, more specifically, a process for nitrating toluene to dinitrotoluene. The process involves a liquid phase nitration reaction of anhydrous nitric acid and toluene in a molar ratio of between about 5:1 and about 9:1 of nitric acid to toluene in a reactor at a reaction temperature of between about 40° C. and about 70° C., in the absence of sulfuric acid and in the absence of any dipolar organic solvent, to produce a mixture containing dinitrotoluene, and isolating said dinitrotoluene by contacting said mixture with a phase separating effective amount of an alkali or alkaine earth metal nitrate salt to cause phase separation of said dinitrotoluene.

7 Claims, No Drawings

PROCESS FOR THE PRODUCTION OF DINITROTOLUENE

This application is a continuation-in-part of co-pending U.S. Application Ser. No. 210,549 filed on June 22, 1988.

FIELD OF THE INVENTION

This invention relates generally to aromatic nitration reactions and, more specifically, to a process for nitrating toluene to dinitrotoluene.

BACKGROUND OF THE INVENTION

Nitration reactions of aromatic hydrocarbons are generally conducted in mixed acid systems, such as mixed nitric and sulfuric acids. However, these mixed acid systems usually involve reconcentration of the spent sulfuric acid after the nitration reaction. This reconcentration step is time consuming, energy intensive and requires the use of expensive materials of construction. In addition, the use of sulfuric acid tends to result in significant nitrocreosol and cyanide by-product formation which requires expensive waste-water treatment to remove.

In view of these disadvantages associated with mixed nitric/sulfuric acid systems, there have been recent attempts to perform gas phase or liquid phase nitrations in concentrated nitric acid in the absence of sulfuric acid. By way of illustration, U.S. Pat. No. 4,064,147 discloses the preparation of aromatic mononitro compounds (such as mononitrobenzene) by a liquid phase reaction with nitric acid having an acid concentration of between 70 percent and 100 percent by weight using a reaction temperature of between 0° C. and 80° C. When employing a relatively reactive compound such as benzene or toluene as a starting material, this patent teaches that a nitric acid concentration of between 70 and 90 percent by weight is preferred. The disclosure of this patent requires a ratio of nitric acid plus water to organic components of not below 3 when using 70 percent nitric acid, and not below 8 when using 100 percent nitric acid. However, it has now been found that such a high acid ratio using 100 percent nitric acid tends to favor dinitro-compound production, not desired by the patentee in the '147 patent.

U.S. Pat. No. 2,362,743 discloses a two-step process for the manufacture of dinitrotoluene ("DNT") in the absence of sulfuric acid which comprises (a) nitrating toluene to mononitrotoluene using a nitric acid having a concentration of from about 60 percent to about 75 percent and a mole ratio of toluene to nitric acid of about 1 to about 3.5 and (b) nitrating the mononitrotoluene to dinitrotoluene using nitric acid having a concentration of from about 90 percent to about 100 percent, and a mole ratio of mononitrotoluene to nitric acid of about 1 to about 3. Although the process of this '743 patent is advantageously conducted in the absence of sulfuric acid, it has now been found that in step (b), a very high percentage of the nitrated product (up to 25 percent) based upon the amount of toluene reactant employed does not phase separate from the nitric acid medium. Indeed, the '743 patent teaches vacuum distillation of the product mixture to isolate the desired dinitrotoluene, an expensive and highly energy intensive process step.

U.S. Pat. No. 3,928,395 discloses a process for nitrating unsubstituted or substituted benzene at a reaction temperature of −40° C. to 80° C. using 90% to 100% nitric acid in the optional and preferred presence of a dipolar aprotic solvent, wherein the reaction is halted by means of a dipolar aprotic solvent.

Since dinitrotoluene is useful as an intermediate in producing TDI, new processes for the selective manufacture of this intermediate would be highly desirable to the polyisocyanate manufacturing community.

SUMMARY OF THE INVENTION

The present invention relates to a process for producing and isolating dinitrotoluene by a liquid phase nitration reaction of anhydrous nitric acid and toluene in a molar ratio of between about 5:1 and about 9:1 of nitric acid to toluene in a reactor at a reaction temperature of between about 40° C. and about 70° C., in the absence of sulfuric acid and in the absence of any dipolar organic solvent, to produce a mixture containing dinitrotoluene, and isolating said dinitrotoluene by contacting said mixture with a phase separating effective amount of an alkali or alkalene earth metal nitrate salt to cause phase separation of said dinitrotoluene.

This and other aspects of the present invention will become apparent upon reading the following detailed description of the invention.

DETAILED DESCRIPTION OF THE INVENTION

In accordance with the process of the present invention, the nitration reaction is conducted using anhydrous nitric acid in the absence of sulfuric acid and in the absence of an organic solvent. Moreover, an organic solvent is not used to halt the reaction. As used herein, the term "anhydrous nitric acid" is intended to designate nitric acid having an acid concentration of between 95 and 100 weight percent, preferably at least 98 weight percent, the remainder being water. It is desirable to minimize the amount of water in the reaction mixture since water causes the nitration reaction to stop at the mononitration stage in toluene reaction.

The process of the present invention utilizes a one-step reaction in a single phase liquid medium and does not involve the formation of the two phase emulsions observed in conventional, mixed sulfuric/nitric acid nitration processes. Following the reaction, the desired dinitrotoluene is isolated by phase separation caused by an alkali metal nitrate or alkaline earth metal nitrate salt. The nitrate salt phase separation agent can be added before, during, or after the reaction, and the effect is to cause the single phase product mixture to separate into two phases, one phase containing water and unreacted nitric acid and the other phase containing dinitrotoluene. Illustrative phase separation agents are, for example, the sodium, potassium, calcium, or magnesium nitrate salts, preferably magnesium nitrate hexahydrate or magnesium nitrate trihydrate, the latter being most preferred.

Another surprising aspect of this invention is that the reaction can be conducted under moderate reaction conditions to provide an excellent yield of the desired dinitrotoluene product. Thus, the reaction is suitably conducted at a reaction temperature of between about 40° C. and about 70° C., more preferably between 50° C. and 70° C. The reaction is suitably conducted at atmospheric pressure, although superatmospheric pressure can be employed if desired. The reaction time is typically less than five hours, preferably less than two hours, and more preferably less than one-half hour.

The molar ratio of nitric acid plus water to toluene employed in the reaction is generally between about 5:1 and about 9:1, preferably between 6:1 and 9:1, more preferably between 7:1 and 9:1, most preferably 8:1.

Operating within the above-recited broad ranges of molar ratios (and particularly within the preferred ranges) maximizes the production of the desired product and minimizes by-product formation.

After reaction and product formation, it is desired to maintain the product mixture at an elevated temperature, preferably a temperature of between about 65° C. and about 75° C. to assist in the rapid dissolution of the phase separation agent in the product mixture. The phase separation agent is generally incorporated into the mixture of dinitrotoluene and unreacted nitric acid in a "phase separation effective amount", i.e., an amount sufficient to cause phase separation of the mixture in order to facilitate isolation of the dinitrotoluene from the unreacted nitric acid in the product mixture. Preferably, the phase separation agent is employed in an amount of between 0.5 weight percent and 1.5 weight percent (more preferably about one percent) per one weight percent of nitric acid plus water present in the product mixture. The reaction is preferably conducted in a distillation still, and in such an apparatus the phase separation agent will cause separation of the DNT from the distillation still bottoms.

Washing with water and a basic solution produces a purified DNT product. These wash waters are free of the nitrocresol impurities observed in the wastewater produced in a conventional, mixed sulfuric/nitric acid DNT process. The aqueous nitric acid from the phase separation step can be purified by toluene extraction, the toluene phase being recycled to the reaction step and the 60–70% aqueous nitric acid phase reconcentrated, sold or used in other product manufacture.

The following examples are intended to illustrate, but in no way limit the scope of, the present invention.

EXAMPLE 1

Synthesis and Isolation of Dinitrotoluene (1) Reaction: To a 100ml, jacketed flask equipped with septum adapter, magnetic Stir bar, thermometer and $N_2$ line, was added 60.0g of 98% $HNO_3$ (0.933 mole). After heating the $HNO_3$ to 54° C. with hot water to the reactor jacket, toluene (10.75g, 0.117 mole) was fed by syringe at 0.40 ml per minute, employing a Sage Instrument syringe pump. The reaction temperature rose to 60° C. within 2 minutes and was maintained to 60° C. after toluene addition was complete by adjusting the water jacket temperature. Periodic sample aliquots indicated complete toluene to DNT conversion in 27 minutes, following the completion of the toluene feed.

Other reaction mixtures and conditions gave the following reaction times to completion:

| Temperature, °C. | $HNO_3$/Toluene Mole Ratio | Time to Completion |
| --- | --- | --- |
| 50 | 7:1 | 4.5 hr |
| 60 | 7:1 | 2.0 hr |
| 70 | 7:1 | 1.25 hr |
| 50 | 8:1 | 50 min |
| 60 | 8:1 | 27 min |
| 70 | 8:1 | 16 min |
| 50 | 9:1 | 12 min |
| 70 | 9:1 | 4 min |

(2) Phase Separation: To a solution of 50.46g of 75% $HNO_3$ and 51.40g of dinitrotoluene (mixture of isomers) in a separatory funnel at 70° C. was added 75.09g of magnesium nitrate hexahydrate. After shaking to dissolve the salt, the DNT readily phase separated from the acid/salt mixture. The phases were separated to 112.93g of heavy $HNO_3$/Mg salt phase and 62.17g of the lighter DNT phase. After water dilution of the acid/salt layer and chilling, 1.45g of DNT was recovered. By back calculation, the DNT phase thus contained about 12.2g of aqueous $HNO_3$/Mg salt mixture.

EXAMPLE 2

Reaction and Phase Separation In A Single Pot to Produce DNT

To a 1 liter jacketed reaction flask equipped with a mechanical agitator, thermometer, $N_2$ line and an addition funnel was added 900.14g (14.0 mole) of 98% $HNO_3$ After warming to 50° C., 184.3g of toluene (2.0 mole) was added dropwise to the $HNO_3$. Toluene feed rate and water jacket temperature were adjusted to maintain a 60± 3° C. reaction temperature during the 1.0 hour toluene addition time. After all of the toluene had been fed, periodic sample aliquots indicated complete toluene to DNT conversion in 2.0 hours. The pale orange reaction solution was transferred to a 2 liter flask and excess $HNO_3$ removed by vacuum distillation at 55°–70° C. and 55–80 mm Hg. Upon completion of the distillation, the receiver contained 376.7g of pale yellow 90% $HNO_3$, while there remained 610.2g of yellow DNT/aqueous $HNO_3$ solution in the pot. To the pot solution was added 246.0g of magnesium nitrate hexahydrate, which dissolved when heated to 75° C. with stirring. The now two phase mixture was transferred to a hot separatory funnel and 384.1g of heavy $HNO_3$/Magnesium salt layer drawn off (later found to contain 6.7g of DNT). The DNT layer was washed with water, sodium carbonate solution and again with water to yield 473g of wet DNT. Gas chromatographic analysis of the DNT showed it was free of mono- and trinitrotoluene species. Gas chromatography/mass spectrometric analysis of the base wash layer indicated it was free of nitrophenol species.

What is claimed is:

1. A process for producing and isolating dinitrotoluene which comprises the steps of:
   (a) conducting a liquid phase nitration reaction of anhydrous nitric acid and toluene in a molar ratio of between about 5:1 and about 9:1 of nitric acid to toluene in a reactor at a reaction temperature of between about 40 C. and about 70 C., in the absence of sulfuric acid and in the absence of any dipolar organic solvent, to produce a mixture containing dinitrotoluene, and
   (b) isolating said dinitrotoluene by contacting said mixture with a phase separating amount of an alkali metal or alkaline earth metal nitrate to cause phase separation of said dinitrotoluene.

2. The process of claim 1 wherein said molar ratio is between about 6:1 and about 9:1.

3. The process of claim 1 wherein said phase separation agent is incorporated into said mixture in an amount of between about 0.5 and about 1.5 weight percent of phase separation agent per weight percent of nitric acid plus water in said mixture.

4. The process of claim 1 wherein said reaction temperature is between about 50° C. and about 70° C.

5. The process of claim 1 wherein said reaction employs a reaction time of less than five hours.

6. The process of claim 1 wherein said reaction employs a reaction time of less than one-half hour.

7. The process of claim 1 wherein said phase separation is effected at a temperature of between about 65° C. and about 75° C.

* * * * *